(12) United States Patent
Schmidt et al.

(10) Patent No.: US 7,959,865 B2
(45) Date of Patent: Jun. 14, 2011

(54) MINIATURIZED GAS CHROMATOGRAPH AND INJECTOR FOR THE SAME

(75) Inventors: Tobias Schmidt, Steinhorst (DE); Mathias Mahnke, Guester (DE); Uwe Lehmann, Hamburg (DE)

(73) Assignee: SLS Micro Technology GmbH, Hamburg (DE)

( * ) Notice: Subject to any disclaimer, the term of this patent is extended or adjusted under 35 U.S.C. 154(b) by 905 days.

(21) Appl. No.: 10/541,145

(22) PCT Filed: Jan. 14, 2004

(86) PCT No.: PCT/DE2004/000035
§ 371 (c)(1),
(2), (4) Date: Jan. 3, 2006

(87) PCT Pub. No.: WO2004/065955
PCT Pub. Date: Aug. 5, 2004

(65) Prior Publication Data
US 2006/0210441 A1 Sep. 21, 2006

(30) Foreign Application Priority Data
Jan. 16, 2003 (DE) .................................. 103 01 601

(51) Int. Cl.
*G01N 30/00* (2006.01)
(52) U.S. Cl. .......... 422/89; 422/70; 73/19.02; 73/23.35; 73/23.36; 73/23.37; 73/23.38; 73/23.39; 73/23.4; 73/23.41; 73/23.42; 73/61.52; 73/61.53; 73/61.54; 73/61.55; 73/61.56; 210/659; 95/89; 95/105
(58) Field of Classification Search .................. 73/19.02, 73/23.35–23.42, 61.56; 210/659; 422/89, 422/70; 95/89; 96/105
See application file for complete search history.

(56) References Cited

U.S. PATENT DOCUMENTS

| | | | | |
|---|---|---|---|---|
| 3,201,922 A | * | 8/1965 | Villalobos | 95/86 |
| 3,489,011 A | * | 1/1970 | Firman et al. | 73/863.73 |
| 3,748,833 A | * | 7/1973 | Karas et al. | 96/105 |
| 3,800,602 A | * | 4/1974 | Jones | 73/23.42 |

(Continued)

FOREIGN PATENT DOCUMENTS
DE  103 15 282 A1  10/2004

OTHER PUBLICATIONS

Feustel, A. et al., "A Micro Mass Spectrometer," *Sensor Kongressband*, 1995, pp. 465-470.

(Continued)

*Primary Examiner* — Jill Warden
*Assistant Examiner* — Shogo Sasaki
(74) *Attorney, Agent, or Firm* — Saliwanchik, Lloyd & Eisenschenk (57) ABSTRACT

The invention relates to a miniaturized gas chromatograph and injector for the same. Said micro-GC is compact and simple and economical to construct. Dead volumes are largely avoided in order to achieve reliable and reproducible measured results. Said miniaturized gas chromatograph comprises at least one injector, one separation column and a detector which are combined on a circuit board to give a gas chromatography module. The injector comprises a first sheet with channels, which is provided with a second sheet with channels and which may be displaced relative to the latter, whereby at least one of the sheets is provided with a layer of plastic, in particular a chemically inert plastic on the side of the sheet facing the other side.

9 Claims, 6 Drawing Sheets

U.S. PATENT DOCUMENTS

| | | | | |
|---|---|---|---|---|
| 3,916,465 A | * | 11/1975 | Jones | 73/23.42 |
| 4,474,889 A | | 10/1984 | Terry et al. | |
| 4,493,476 A | | 1/1985 | Strickland et al. | |
| 4,869,282 A | * | 9/1989 | Sittler et al. | 137/15.01 |
| 5,178,190 A | | 1/1993 | Mettner | |
| 5,909,078 A | | 6/1999 | Wood et al. | |
| 5,958,227 A | * | 9/1999 | Uematsu | 210/198.2 |
| 2002/0176804 A1 | | 11/2002 | Strand et al. | |
| 2004/0223282 A1 | | 11/2004 | Bolz et al. | |

OTHER PUBLICATIONS

Feustel, A. et al., "A Microsystem Mass Spectrometer," *Micro Total Analysis Systems*, 1994, pp. 299-304.

Lehmann, U., "Analysis in miniature," *Vacuum Solutions*, Nov./Dec. 1998, pp. 13-15.

Lehmann, U., "Autarky Gas Chromatographic System Realized in MEMS Technology on a Credit Card-Sized Board," *Abstracts Pittcon*, 2005, 180-9.

Lehmann, U. et al., "A micro gas chromatograph based on a plasma polymerized siliconorganic stationary phase," *Sensor Kongressband II*, 1997, pp. 151-153.

Lehmann, U. et al., "Micro machined analytical gas chromatograph with a plasma polymerised stationary phase," *Sensor Proceedings II*, 2001, pp. 487-492.

Lehmann, U. et al., "Micro machined gas chromatograph based on a plasma polymerised stationary phase," *Micro Total Analysis Systems*, 2000, pp. 167-170.

Lehmann, U. et al., "A Miniaturised Gas Chromatographic Module on a Credit Card Sized Motherboard," *Sensor Proceedings*, 2003, pp. 157-161.

Lehmann, U. et al., "A miniaturized gas chromatograph for autonomous and longtime measurements," *Sensor Proceedings I*, 1999, pp. 155-158.

Lehmann, U., "A Packed Column Realized on a 1 $cm^2$ Sized Silicon Glass Chip for Permanent Gas Separation," *Abstracts Pittcon*, 2005, 1910-5P.

Lehmann, U., "World's Smallest, Self-Sufficient Gas Chromatography Module from SLS Micro Technology," *Abstracts Pittcon*, 2004, 1100-100.

"Small is Beautiful," *The Column*, Jul. 2005, pp. 22-23.

Petzold, G. et al., "A Micro Mass Spectrometer," *Micro Total Analysis Systems*, 2001, pp. 224-226.

Siebert, P. et al., "Processing of Complex Microsystems: A Micro Mass Spectrometer," *Symposium on Design, Test, and Microfabrication of MEMS and MOEMS*, Mar.-Apr. 1999, vol. 3680, pp. 562-571, Paris, France.

Siebert, P. et al., "Surface microstructure/miniature mass spectrometer: processing and applications," *Appl. Phys. A*, 1998, vol. 67, pp. 155-160.

Ngo, H.D., et al. "A hybrid micro valve for active flow control" *Conference Proceedings*, 2001, pp. 239-244, vol. 2.

\* cited by examiner

MINIATURIZED GAS CHROMATOGRAPH AND INJECTOR FOR THE SAME

This application is a National Stage Application of International Application Number PCT/DE2004/000035, filed Jan. 14, 2004; which claims priority to German Application No. 10301601.5, filed Jan. 16, 2003.

The invention relates to a miniaturized gas chromatograph and an injector for the same.

Efforts have been made for many years to miniaturize analysis systems for the purpose of handling them with greater ease, increasing the versatility of their application and manufacturing them more cost-effectively. Thus in 1979, S. C. Terry et al. (IEEE Transactions on Electron Devices 26, 1880-1886) described a miniature gas chromatograph fabricated on a silicon wafer.

In many cases, the miniaturized analysis systems used so far, when compared to corresponding devices of the conventional overall size, lack the required accuracy and reproducibility of the analysis results. This deficiency is based particularly on the fact that a truly integrated system was missing so far in which all substantial components, such as for instance the injection system, the separation column and the detector were manufactured using the micro system and/or the MEMS technology (MEMS=micro-electro-mechanical systems) and were adapted to the special requirements in the micro sector. While it is particularly important to avoid dead volumes in the context of gas chromatography, it is also important that the energy requirement is as low as possible in order to enable the manufacturing of hand-held units that can be used directly on site, for instance, in case of a toxic gas alarm.

A miniaturized gas chromatograph is suggested in the patent application DE 19726000. This micro gas chromatograph provides a separation column manufactured using micro system technology with an integrated thermal conductivity detector (TCD) wherein the separation column has a stationary phase that is applied by the plasma polymerization of organic monomers in the entire periphery of the depression. It is possible to obtain reproducible analysis results with the help of this separation column. The gas chromatograph pursuant to the patent application DE 19726000 also provides an injection system with miniaturized ball valves as suggested by Lehmann et al. (2000, Micro Total Analysis Systems 2000, 167-170). In such an injection system however, there can be an incidence of dead volumes. As a result an adverse effect on the measured results cannot be ruled out in the gas chromatograph described in the patent application DE 19726000.

Additional miniature gas chromatographs provide injection systems in which diaphragm valves are used. Such systems have been described by Terry et al. (1997, IEEE Transactions on Electron Devices 26, 1880-1886), J. B. Angell et al. (1983, Scientific American 248, 44-55) as well as in the patent applications WO 96/27792, WO 90/06470 and EP 0512521. Problems occurred frequently even in these gas chromatographs, since the injection systems used can have comparatively large dead volumes. Apart from that, the described systems are relatively complex, difficult to manufacture and comparatively expensive.

The object of the present invention is to provide an analysis system that is compact, and simple and economical to construct and in the use of which dead volumes are largely avoided in order to achieve reliable and reproducible measuring results. In particular, an injection system should be provided that is comparatively simple to manufacture using MEMS technology and enables the reliable and reproducible introduction of a defined sample quantity to the separation column of a miniature gas chromatograph.

This object is achieved by the characteristics specified in the subject matter of claim 1.

The miniaturized gas chromatograph pursuant to the invention comprises at least one injector, one separation column and a detector, which are combined on a circuit board to give a gas chromatography module. The injector comprises a first sheet with channels, which is provided with a second sheet with channels and which may be displaced relative to the latter, whereby at least one of the sheets is provided with a layer of plastic, in particular a chemically inert plastic on the side of the sheet facing the other sheet.

In the context of the present invention, the term "plastic" refers to any material whose essential components consist of such macromolecular organic compounds that are derived synthetically or by modifying natural products (refer Römpp Chemistry Lexicon, 9. edition, page 2398).

In the gas chromatograph pursuant to the invention, the GC components of injector, separation column and detector are combined on a circuit board in the form of a module. This compact construction can effectively avoid dead volumes. The components are manufactured preferably using MEMS technology. Printed circuit boards such as those used for computers can be used in this context. However, they should be able to withstand the resulting temperatures that are comparatively high. A type of slide valve is implemented in the injector using micro-system technology with the help of which it is possible to introduce a defined volume of a liquid or gaseous sample reliably and reproducibly to the downstream connected separation column.

The principle of such slide valves is basically well-known to prior art and is described for instance in patent applications DE 1167564, DE 1190697, DE 1673157, and EP 0225779 even for gas chromatographs. Problems related to impermeability can occur in the use of such slide valves. However, slide valves are frequently used in "classic" gas chromatography since the resulting problems related to impermeability cannot influence the system performance decisively. However, the slide valves described in the aforementioned patents are not suitable for a gas chromatograph fabricated using in micro system technology.

In the patent application DE 10125123 a miniaturized chemical laboratory with a multitude of reactors and gas chromatographs assigned to these is described in which samples from the reactors are provided to the separation columns of the chromatographs using a slide valve. Even this slide valve is not manufactured using micro system technology and hence has decisive disadvantages. In particular, the stainless steel used is comparatively heavy. The motor that is not described in detail in the patent application DE 10125123 for actuating the injector 1 may have a comparatively high energy requirement due to the drive force required. Stainless steel is by all means more unsuitable for the manufacturing of microsystems than for instance, silicon. Even in the case of the valve pursuant to the patent application DE 10125123 problems related to impermeability can hardly be avoided if sample components get deposited between the channel sheets.

On the other hand, the gas chromatograph pursuant to the invention comprises an injector that is fabricated using micro system technology and hence can be operated using lesser drive force and consequently has a lesser energy requirement. The impermeability of the system even in the case if high pressure can be ensured by providing at least one of the sheets with a layer of a preferably chemically inert plastic. The plastic is substantially more flexible than for instance stainless steel and can seal off effectively even if small sample particles enter between the sheets. It is advantageous if the surfaces of both the sheets facing one another, i.e. the surfaces that slide past one another when the injector is actuated, are coated with plastic.

The coating of plastic is preferably applied by the plasma polymerization of organic monomers, wherein difluoromethane, hexafluorobutadiene and/or octafluorocyclobutane can be used as starting compounds. During the plasma polymerization, gaseous monomers that are stimulated using a plasma condense on a substrate as high cross-linked layers. The structure and degree of cross-linking can be controlled by a variation in the process parameters such as pressure, gas flow and energy supply. With the help of the plasma polymerization, the use of the aforementioned starting monomers results in particularly thick, chemically, mechanically and thermally stable layers. It is particularly preferable if the plastic layer is a PTFE (polytetrafluoroethylene)-type of antiadhesive chemically inert layer. Sample particles do not remain stuck to such a coating and therefore cannot result in impermeability of the injector. Even if a particle does enter between the sheets and remains stuck there, this usually does not lead to problems related to impermeability, unlike in the use of steel, because the plastic is comparatively flexible and is capable of enclosing the particle. Moreover, such a layer being heat resistant enables a permanent operation at for instance 260° C.

The sheets forming the slide valve are preferably made out of silicon. This makes it possible to fabricate the very fine channels in the sheets using the conventional off-the-shelf technology such as the micro system technology, for instance, etching (KOH etching, chemical-physical plasma etching). This also helps to maintain a very low possibility of dead volumes.

The plastic preferably has a lower coefficient of static friction than silicon. The coefficient of static friction $\mu_h$ of silicon on silicon (Si—Si) amounts to around 0.2. As opposed to that, the coefficient of static friction $\mu_h$ of PTFE on PTFE (PTFE-PTFE) is 0.04 and therefore much lower. Coating both the sheets with a PTFE-type of plastic layer results in a lower static friction than in the case of uncoated silicon sheets or in the case of coating only one sheet with the plastic layer. This is particularly advantageous in order to keep as low as possible the energy input that is required for the sheets to slide past one another when the injector is actuated. Although the sheets are pressed onto one another for the purpose of keeping the system leak-proof, it is possible to use a valve drive that has a comparatively low drive force. Thus, for instance, a drive force of approximately 0.2 N is sufficient for the purpose of actuating the injector of the gas chromatograph pursuant to the invention. A corresponding electromechanic drive that can also be fabricated using micro-system technology is, for instance, a linear motor or an electromagnet in the form of a bistable magnet system.

In a first preferred embodiment, an electronic control and evaluation unit is additionally provided on the circuit board. In this manner even the control and evaluation unit is integrated into the GC module. The control electronics can control the temperature of a possible injector- and/or separation column- and/or detector heating. In addition, it can also control the switching mechanism of the injector. By integrating an evaluation unit into the GC module it is possible using the miniature gas chromatograph to evaluate the result on site. The evaluation unit can comprise a result memory in which the measurements can be buffered. Furthermore, it can comprise a database with characteristic data (e.g. retention times) of substances to be measured so that by comparing the measuring data with the characteristic data from the database, it is possible to identify the components of a sample even on site.

In a second preferred embodiment of the invention, the injector and/or the separation column and/or the detector can be temperature-controlled using heating elements. This facilitates the transfer of liquid samples into the gas phase at the suitable temperature and thus enables their analysis using a gas chromatograph. In this context it must be mentioned that even heating elements on ceramic substrates fabricated using thick film technology can be used effectively. In order to protect the control and evaluation unit placed on the circuit board from the heat emitted by the heating elements, recesses are provided in the circuit board. These can be simple depressions that are inserted into the surface of the circuit board. The surprising result of this arrangement is that this simple measure is sufficient for the purpose of preventing the heat emitted from the heating elements from flowing toward the electronics of the circuit board. It is thus not required to undertake additional measures such as mounting a thermal barrier in the form of a layer made of heat-insulating material. The electronic components remain in a temperature range that ensures their reliable functioning.

In a third particularly preferred embodiment of the invention, the first sheet with respect to which the second sheet is displaced is covered by a glass sheet, preferably a borosilicate glass sheet. This particularly facilitates the fabrication of the required channels. Channels are etched in the surface of the silicon wafer in the form of open depressions. The depressions are covered using the glass disk that can be mounted directly on the silicon wafer by means of anodic bonding. By creating the corresponding depressions in the surface of the glass disk, for instance using lithographic etching processes or boreholes, tubular channels are formed into which the capillaries can be inserted for the purpose of establishing the connection to the carrier gas and/or the sample gas stream. The additional advantage of the use of the chemically very stable borosilicate glass is that the channels are clearly visible, making it possible to recognize possible deposits visually.

The first sheet comprises at least three channels, the second sheet at least two supply channels and two discharge channels. However, it is also possible to provide additional channels, for instance a second sample gas channel or a reference gas channel. As a rule, the sheet that is displaced relative to the other sheet comprises at least one supply or discharge channel more than the other sheet.

In a fourth embodiment recesses, such as depressions are provided in the circuit board into which capillaries preferably glass capillaries are countersunk for the purpose of the gas flow. In this manner it is possible to avoid laying gas flow pipes on the surface of the circuit board. Moreover, this also helps to effectively prevent any tearing or snapping of the gas pipes for instance while handling the GC module. In addition to that, it also substantially facilitates a possible temperature-control of the gas pipes. Corresponding heating elements can be easily arranged in the recesses in the circuit board.

In a fifth preferred embodiment, the detector is provided, that is preferably a thermal conductivity detector, with a gas flow sensor. The detector has a gas flow sensor connected upstream in the flow direction of the gas through the separation column. Such an arrangement enables the correction of the base lines easily by suitably setting the signal of the gas flow sensor against that of the detector.

The present invention also relates to an injector, particularly for a miniaturized gas chromatograph that comprises a first sheet with channels, which is provided with a second sheet with channels and which may be displaced relative to the latter, whereby at least one of the sheets is provided with a layer of plastic, on the side of the sheet facing the other sheet. The plastic is preferably chemically inert for the purpose of largely ruling out the possibility of an interaction with the sample components.

The injector is fabricated using micro-system technology and is suitable for microsystems into which liquid or gas streams are conveyed and using which a defined liquid or gas volume is inserted into a liquid or gas stream. For instance, the injector is suitable for use in a gas chromatograph, besides being used advantageously in other chromatographs such as liquid chromatographs.

The layer made out of plastic is preferably applied by the plasma polymerization of organic monomers wherein organic monomers such as difluoromethane, hexafluorobutadiene and/or octafluorocyclobutane are used as starting compounds. The result is a particularly thick and stable layer that increases the versatility of use of the injector. Thus it is possible to use an injector permanently under high pressure and at high temperature with less wear and tear and high impermeability. Moreover, this layer with its corresponding surface energy involves a low possibility of interaction with reagents.

For the purpose of actuating the injector easily, it is advantageous if the plastic has a lower coefficient of static friction than the silicon. This enables the use of silicon as the material for the sheets without having to employ a high drive force for actuating the valves. Thus even the drive for actuating the injector i.e. for displacing the first sheet relative to the second, can be dimensioned such that it is possible and practical to use an electromechanic drive that is fabricated using micro-system technology. For instance, linear motor or a bistable magnet system can be used here.

The present invention is exemplified in greater detail herein below on the basis of FIGS. 1 to 6. Shown are.

Figure 1:
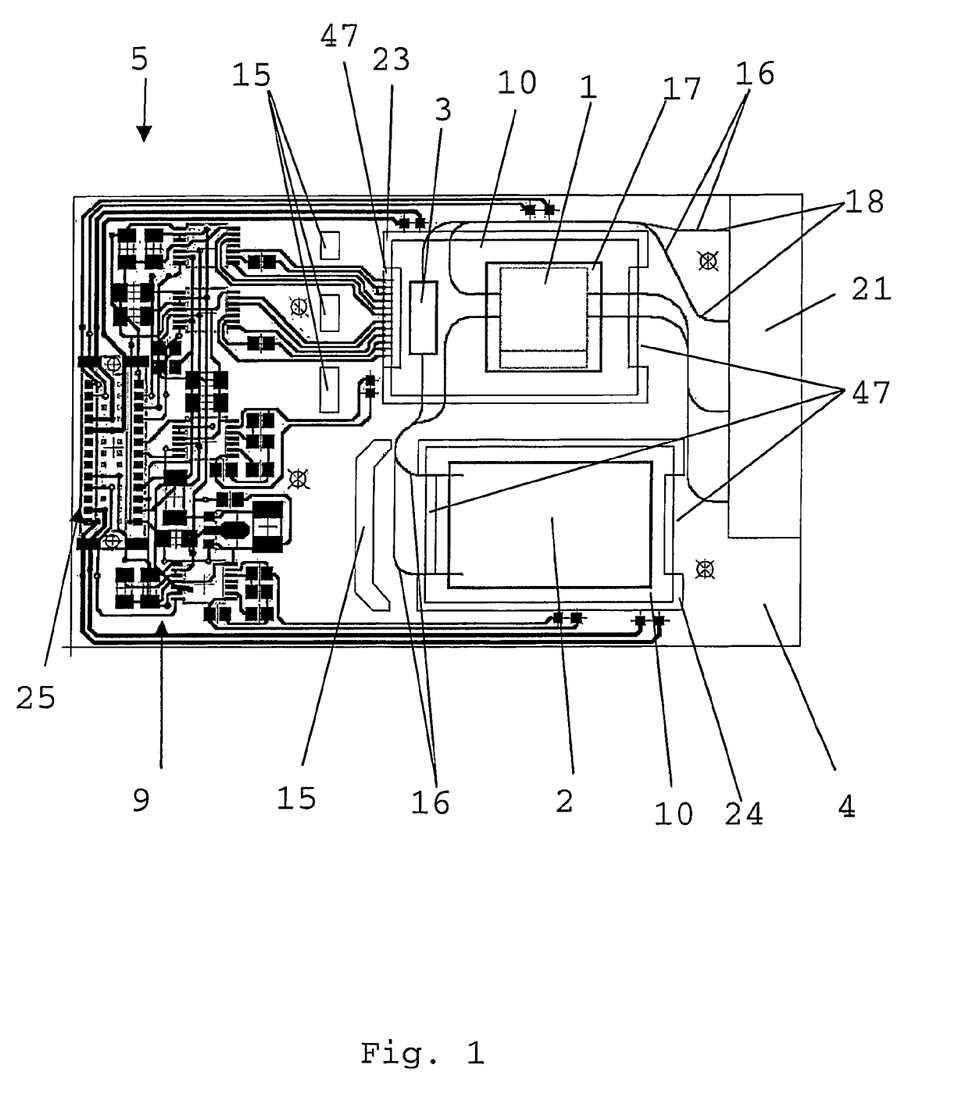
FIG. 1 is a top view of a first embodiment of a GC module of a miniature gas chromatograph.

Referring now in more detail to the drawings FIG. 1 illustrates a GC module 5 for the gas chromatograph pursuant to the present invention. The GC module comprises a circuit board 4. The circuit board is preferably one that is able to withstand the occurring high temperatures. Such circuit boards are available in specialist stores. Recesses 23, 24 are provided in the circuit board 4 into which the injector 1 with the electromechanic drive 17, here a linear motor, the detector 3 that is a thermal conductivity detector, as well as the separation column 2 are mounted. The separation column 2, the injector 1 and the detector 3 are provided with heating in the form of heating elements 10, that are ceramic plates here with heating elements fabricated using thick-film technology. Heating elements 10 are also placed in the recesses 23, 24 wherein the heating elements 10 lie on the supporting surfaces 47 formed by the circuit board 4. The surface of the heating elements 10 lying on the supporting surfaces 47 is as small as possible in order to avoid the heat from transferring onto the surface board. Thus the injector can be temperature-controlled to 100° C., the separation column to 200° C. In the illustrated embodiment, a common heating is provided for the injector 1 and the detector 3. However, if necessary, the detector can also be provided with its own heating. Incidentally, it is also possible to provided several detectors 3 that can be heated in common or separately. Similarly, it is also possible to arrange several separation columns on one circuit board. The electronic control and evaluation unit 9 is also mounted on the circuit board 4. This electronic control and evaluation unit 9 controls the heating elements 10, measures the temperature of the injector 1 and the separation column 2, also the temperature of the detector 3, if necessary, records, stores and if required evaluates the measured values supplied by the detector 3. An interface 25 can be used to pass the data to an integrated output unit, for instance, a monitor or even an external device such as a PC or a printer. In order to protect the heat-sensitive electronics on the circuit board from the heat emitted by the heating elements 10, recesses 15 are provided in the circuit board 4. These effectively avoid the heat transfer by convection to the region of the circuit board 4 in which the electronic control and evaluation unit 9 is located. Experiments have proved that additional measures such as application of a layer of a heat-insulating material as a thermal barrier etc. are thus unnecessary. Even during the permanent operation of the gas chromatograph and by accommodating the GC module 5 in a corresponding housing, the electronics remain in a temperature range that ensures its reliable operation. The gas supply and discharge pipes are fabricated in the form of capillaries 18, particularly glass capillaries that are placed in recesses 16 in the circuit board 4. The capillaries 18 start and/or end in a gas distribution block 21 by means of which the carrier gas and the sample can be supplied and discharged. The control and evaluation unit 9 can also be mounted on a separate circuit board.

Figure 2:
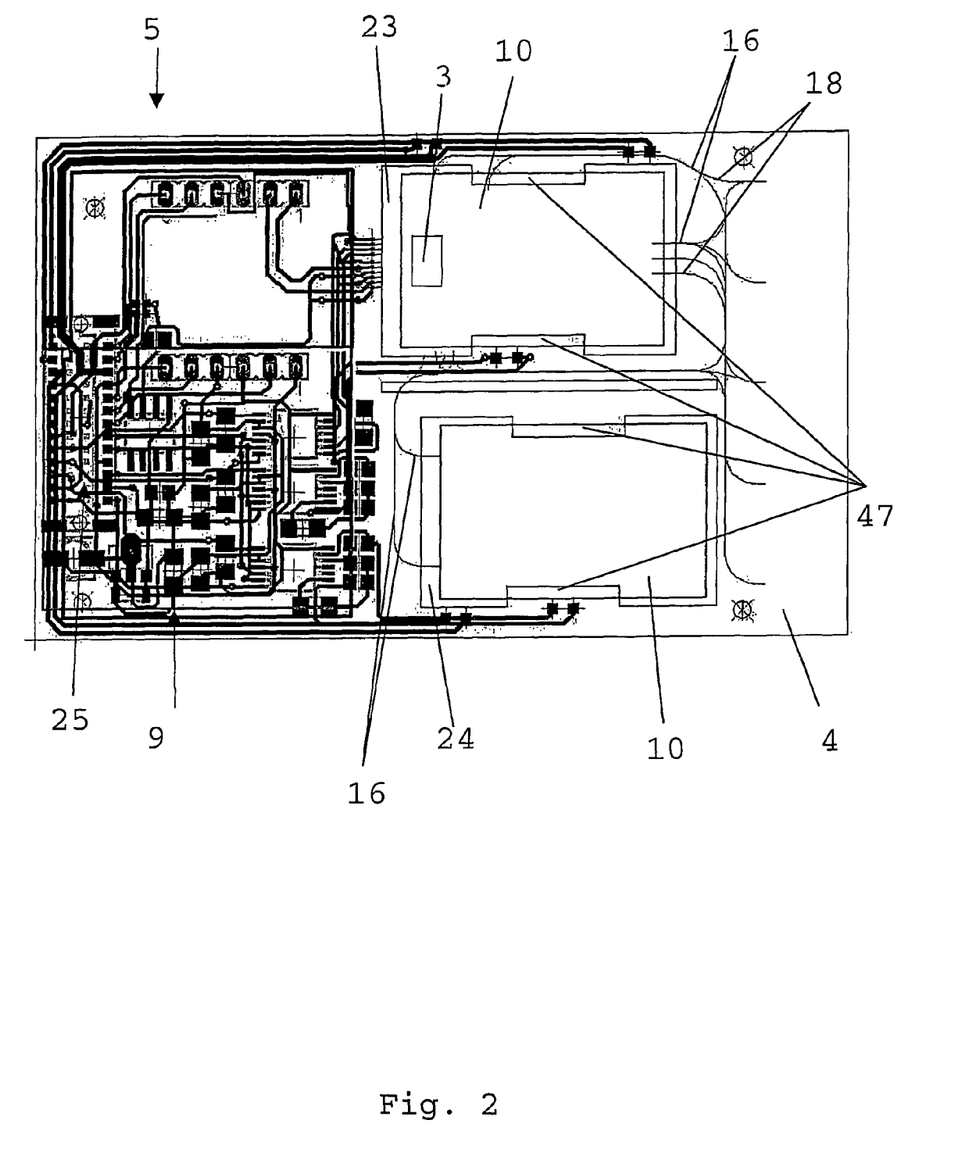
FIG. 2 is a top view of a second embodiment of a GC module of a miniature gas chromatograph.

FIG. 2 illustrates a second embodiment of a GC module 5 for the gas chromatograph pursuant to the invention in a simplified illustration. Here, as opposed to the embodiment illustrated in FIG. 1, the supporting surfaces 47 are arranged in such a manner that the flow of the heat from the heating elements 10 conducted by the supporting surfaces 47 is led away from the control and evaluation unit 9. For this purpose the supporting surfaces 47 are displaced by 90°, so that no supporting surface 47 is arranged for the heating elements 10 in the direction of the control and evaluation unit 9. Moreover, in this manner, the recesses 23, 24 form a thermal barrier for the control and evaluation unit 9 as described above in connection with the recesses 15. Arranging a sufficient distance between the heating elements 10 and the border formed by the circuit board 4 around the recesses 23, 24 effectively avoids the transfer of heat in the direction of the control and evaluation unit 9. Consequently there are no fears regarding any adverse effects on the operation of the electronic components. Therefore in this embodiment, it is also possible to dispense with the recesses 15.

Figure 3:
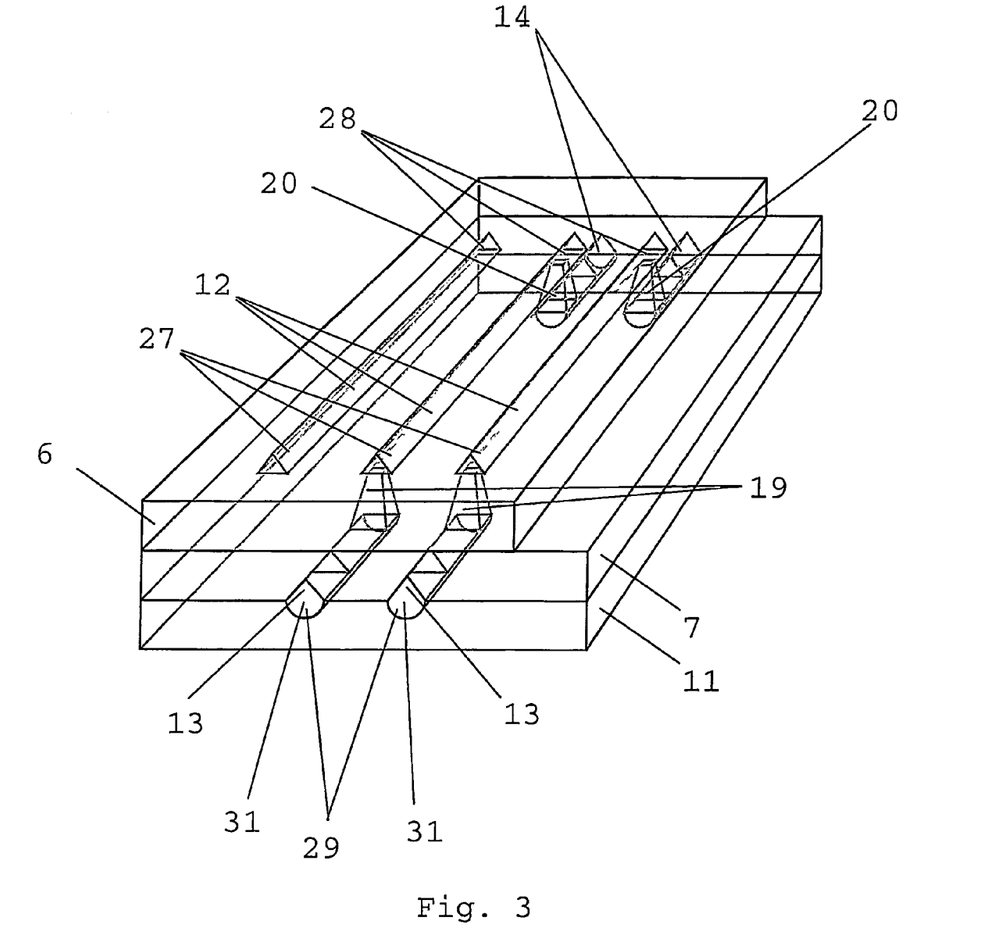
FIG. 3 is a spatial sketch of an embodiment of an injector.
Figure 4:
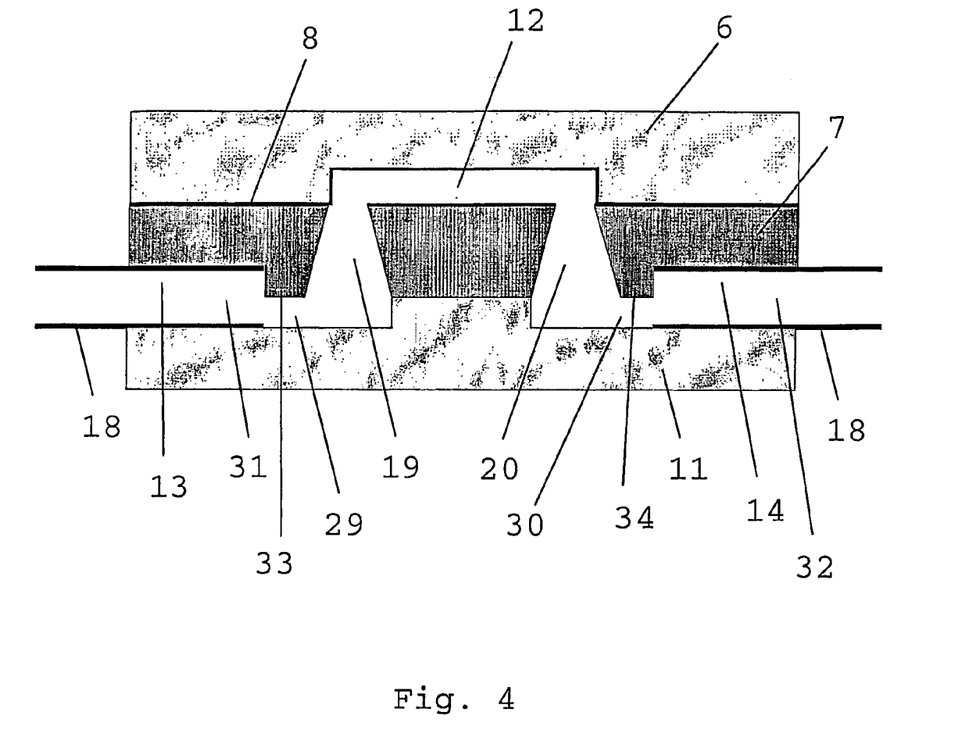
FIG. 4 is a section of the injector illustrated in FIG. 3 along the sample gas pipe or carrier gas pipe.

FIG. 3 illustrates an embodiment of an injector 1 for a gas chromatograph pursuant to the invention. The injector 1 comprises substantially a sheet 7, a sheet 6 and a cover sheet 11. The sheets 6 and 7 are preferably made of silicon. The width of sheet 6 is slightly smaller as compared to that of sheet 7. The surfaces of sheets 6 and 7 lying one on top of the other are coated with a layer 8 of an inert, PTFE-type plastic, wherein the coating is applied by the plasma polymerization of organic monomers for instance difluoromethane, hexafluorobutadiene and/or octafluorocyclobutane. The coating not only provides the injector 1 with sufficient impermeability, but also enables the sheets 6, 7 to slide past one another when the injector 1 is actuated, without necessitating a large energy input for this purpose. In this manner, a linear motor 17 can be used that applies a drive force of approximately 0.2 to 1 N. Using methods that are well-known to those skilled in the field of micro-system technology, three channels 12 are structured on a surface of sheet 6 in the form of depressions. The depressions are open toward one side of the sheet 6. Due to the etching process used, the cross-section of the channels is substantially triangular in shape. However, it can have any other shape, e.g. even a round shape. The channels 12 end inside the sheet 6 and do not lead up to the edges of the sheet 6. Channels 13, 14 are structured on the surface of the sheet 7 using etching processes. As opposed to the arrangement in sheet 6, the channels 13, 14 start at the edge of the sheet 7 and extend from here into a part of sheet 7. Apart from that, through holes 19, 20 are etched in the sheet 7 that extend from the side of sheet 7 facing sheet 6 to the side of sheet 7 facing the cover sheet 11. The etching method used results in a pyramid-shaped design of the through holes 19, 20 with a substantially quadratic cross-section that tapers toward the side of the sheet 7 facing the sheet 6. It is possible by all means to provide through holes 19, 20 of various other designs. The channels 13, 14 lie opposite to one another on the ends of the sheet 7. The through holes 19, 20 lie on the line formed by connecting the centerlines of the channels 13, 14. The sheet 6 is arranged with respect to sheet 7 in such a manner that each of the end regions 27, 28 of the channels 12 lies opposite to the openings formed by the through holes 19, 20 in the sheet 7. The cover sheet 11 is preferably made of borosilicate glass and is firmly connected to the sheet 7 for instance by anodic bonding. Trench-type channels 29, 30 are provided in the surface of the cover sheet 11 in the form of a semi-circular borehole or lithographic etching that start on the edge of the cover sheet 11 and extend into a part of the cover sheet 11. The sheet 7 and the cover sheet 11 are arranged in such a manner with respect to one another that the channels 13, 14 and the channels 29, 30 lie opposite to one another and form channels 31, 32 (refer FIG. 4). As illustrated in FIG. 4, the channels 29, 30 in the cover sheet 11 are longer than the channels 13, 14 in the sheet 7 and thus project further into the interior of the injector 1. The through holes 19, 20 are also slightly displaced in the interior of the sheet 7 so as to form projections 33, 34 that can form a stop for the capillaries 18 inserted in the channels 31, 32. The gas, for instance a carrier gas thus flows by means of the capillary 18 into the channel 31 and the channel 29. By means of the through hole 19 the gas enters into the channel 12 in the sheet 6. By means of the through hole 20 the gas flows into the channel 30, from there into the channel 32 and into the capillary 18 on the other side of the injector 1.

Figure 5:
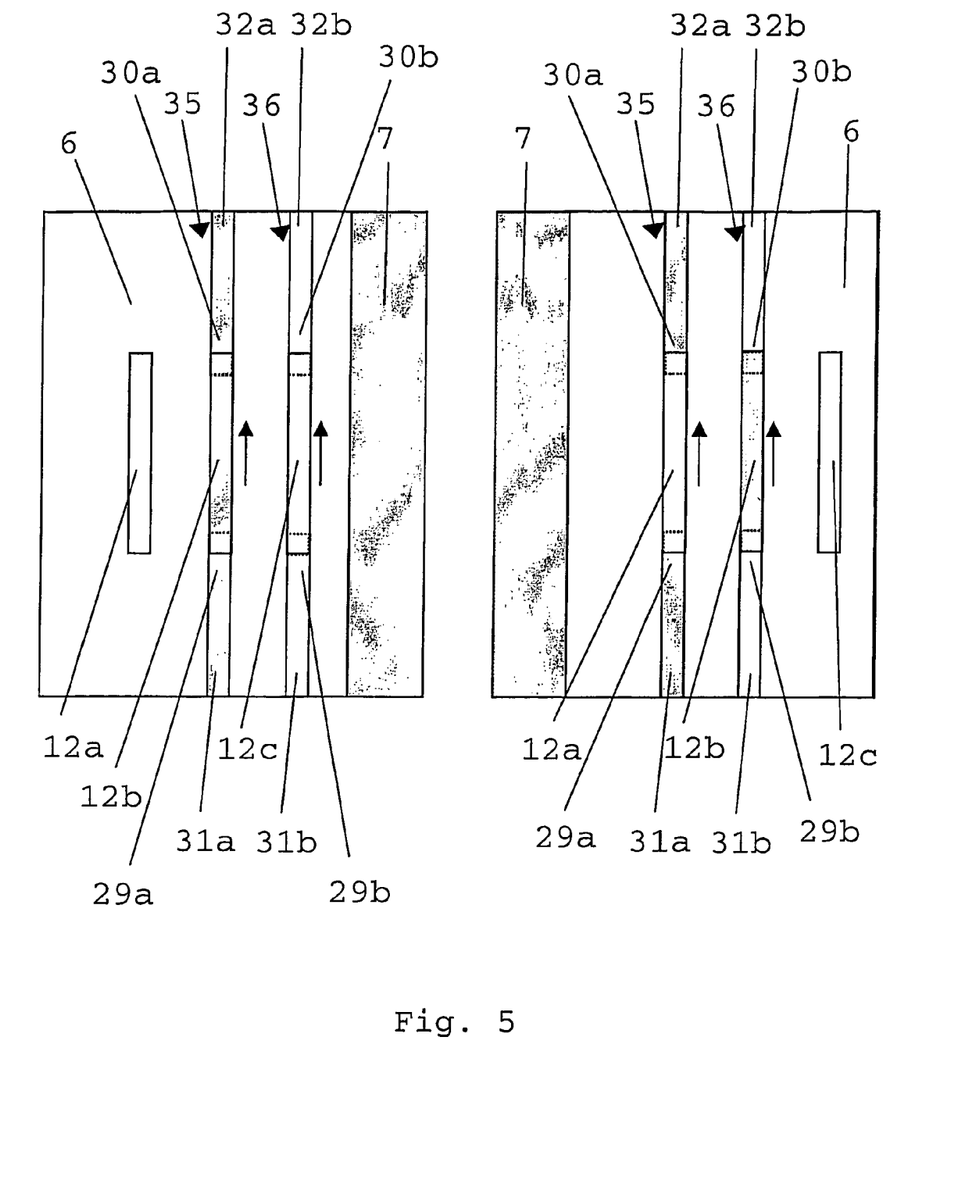
FIG. 5 is the schematic illustration of the top view of an injector illustrated in FIG. 3 that depicts the mode of operation of the injector. Left: first position (rest position) of the injector. Right: Position of the injector following actuation. The arrows mark the sample gas stream and/or carrier gas stream.

FIG. 5 illustrates the mode of operation of the injector 1. In the first position (rest position, FIG. 5, left) the sheets 6, 7 lie in such a manner on top of each other that the channels 31*a*, 32*a*, are connected to one another by means of the channels 29*a*, 30*a*, the through holes 19*a*, 20*a* and also the channel 12*b* and form a channel 35 for the sample gas stream. The channels 31*b*, 32*b* are connected to one another by means of the channels 29*b*, 30*b*, the through holes 19*b*, 20*b* and also the channel 12*c* and form a channel 36 for the carrier gas stream. Following the actuation of the injector 1, the sheet 6 is displaced relative to the sheet 7 (FIG. 5, right). In this second position, the channel 12 connects the channels 31*a*, 32*a*, 29*a*, 30*a* to the through holes 19*a*, 20*a*, while the channel 12*b* connects the channels 31*b*, 32*b*, 29*b*, 30*b* to the through holes 19*b*, 20*b*. In this manner the sample gas volume in channel 12*b* enters into the carrier gas channel 36 and is transported by the carrier gas stream present there onto the separation column 2. The sample volume can be determined by appropriately dimensioning the channel 12. A new measuring cycle can commence after the injector 1 is reset to its rest position. Even additional channels can be provided, for instance, sample gas channels 35 or a reference gas channel for the purpose of injecting sample gas into the carrier gas stream even while resetting the injector 1 or for the purpose of enabling multiple measuring of different samples.

Figure 6:
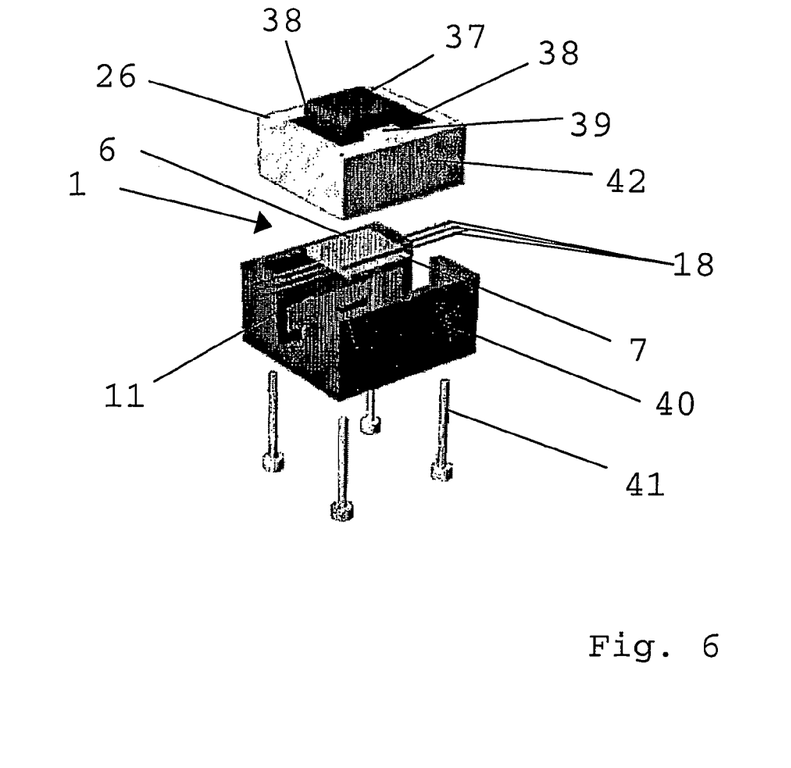
FIG. 6 is an exploded illustration of a linear motor.
Figure 7:
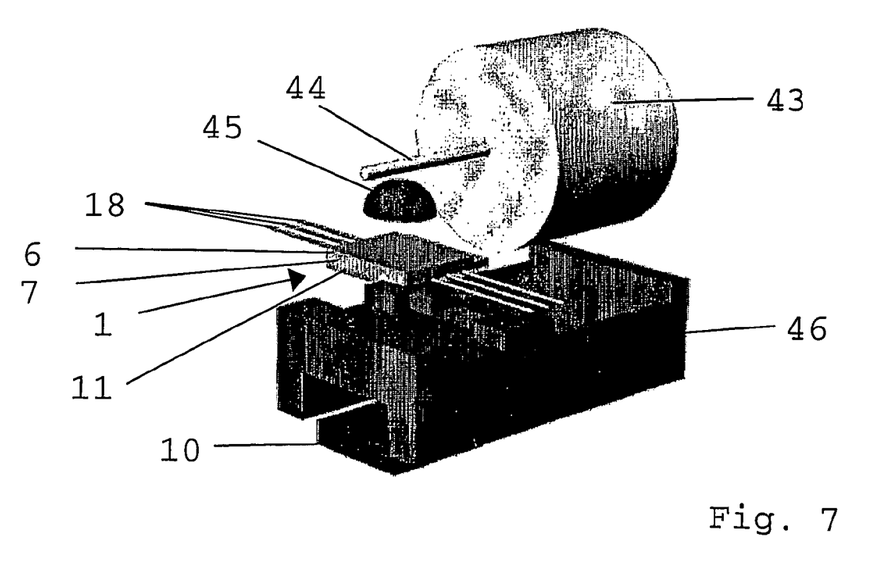
FIG. 7 is an exploded illustration of a bistable magnet system.

FIGS. 6 and 7 illustrate an injector 1 in accordance with the FIGS. 3 to 5 with an electromechanic drive 17 as a linear motor fabricated using micro-system technology (FIG. 6) and/or as a bistable magnet system (FIG. 7). The linear motor 17 comprises a coil 37 and a permanent magnet 38. The coil is moveably mounted on an axle 39 that is formed by a housing part 42 (magnetic yoke). The linear motor 17 can be attached directly with its coil to the sheet 6 or can be fastened mechanically by means of an adapter. When current passes through the coil 37, the latter moves along the axle 39 and displaces the sheet 6 relative to sheet 7 (compare FIG. 5). The injector 1 with the linear motor 17 is located in a housing part 40. The housing part 42 is tightly connected to the housing part 40 by means of screws 41 and boreholes 26. The sheet 7 with the cover sheet 11 is fixed in the housing part 40. In this design, sheet 6 is pressed onto the sheet 7 for the purpose of ensuring sufficient impermeability. Due to the coating of the layer 8 made of plastic the sheet 6 can slide past the sheet 7 without requiring a high drive force for this purpose. The drive force of the magnitude of approximately 0.2 to 1 N provided by the linear motor 17 is sufficient to create the relative movement of the sheet 6. The housing parts 42, 40 can be manufactured by selective laser sintering, in which a laser sinters and/or melts a granule of a particulate starting material. Even plastics can be used in addition to metals and ceramic substances. The advantage of the linear motor 17 is that it is composed of comparatively fewer (five) individual parts.

The electromechanic drive 17 illustrated in FIG. 7 on the form of a bistable magnet system comprises a drive 43 and an axle 44 that is connected to the sheet 6 tightly. An adhesive joint 45 is sufficiently suited for this purpose. When the injector 1 is actuated, the axle 44 moves back and carries the sheet 6 along. Both the drive 43 as well as the injector 1 are placed in a housing 46. Here clamping fixtures ensure that the sheets 6, 7 are pressed onto one another. A recess for a heating element 10 can be provided on the lower side of the housing 46. The bistable magnet system 17 has a slightly more complex design as compared to the linear motor described above. It is composed of a total of ten individual parts. However, the connection to the injector proves to be easier in the case of a bistable magnet system than in the case of the linear motor. In addition, the achievable drive force of the magnitude of approximately 10 N using a bistable magnet system is substantially greater than the achievable drive force in the case of a linear motor.

LIST OF REFERENCE SYMBOLS 1. injector
2. separation column
3. detector
4. circuit board
5. gas chromatography (GC) module
6. sheet
7. sheet
8. layer made of inert plastic 9. electronic control and evaluation unit
10. heating elements
11. glass sheet
12. channel
13. supply channel
14. discharge channel
15. recess
16. recess
17. electromechanic drive
18. capillary
19. through hole
20. through hole
21. gas distributor block
22. capillary
23. recess
24. recess
25. interface
26. boreholes
27. end region
28. end region
29. channel
30. channel
31. channel
32. channel
33. projection
34. projection
35. channel (sample gas)
36. channel (carrier gas)
37. coil
38. permanent magnet
39. axle
40. housing part
41. screws
42. housing part
43. drive
44. axle
45. connection
46. housing
47. supporting surface

The invention claimed is:

1. Miniaturized gas chromatograph comprising at least one injector (1), one separation column (2) and a detector (3) wherein the injector (1), the separation column (2) and the detector (3) are combined on a circuit board (4) to give a gas chromatography module (5), and the injector (1) comprises a first sheet (6) with channels (12) and a second sheet (7) with channels (13) wherein the sheets may be displaced relative to each other, whereby at least one of the sheets (6, 7) is provided with a layer (8) of plastic on the side of the sheet facing the other sheet (7, 6), wherein the layer (8) of plastic is a plasma polymerized layer, further comprising at least one heating element (10) configured such that one or more of the injector (1), the separation column (2) and/or the detector (3) can be temperature-controlled, and further comprising an electronic control and evaluation unit placed on the circuit board and a plurality of recesses (15, 23, 24) provided in the circuit board (4) such that the electronic control and evaluation unit (9) is protected from the heat emitted by the heating elements (10).

2. Miniaturized gas chromatograph pursuant to claim 1, wherein the plastic is chemically inert.

3. Miniaturized gas chromatograph pursuant to claim 1, wherein the layer is a plasma polymerized layer of organic monomers selected from difluoromethane, hexafluorobutadiene, or octafluorocyclobutane.

4. Miniaturized gas chromatograph pursuant to claim 1, wherein the sheets (6, 7) are made of silicon.

5. Miniaturized gas chromatograph pursuant to claim 1, wherein the plastic has a lower coefficient of static friction than silicon.

6. Miniaturized gas chromatograph pursuant to claim 1, wherein at least one heating element (10) comprises ceramic plates with heating elements made via thick film technology.

7. Miniaturized gas chromatograph pursuant to claim 1, wherein the second sheet (7) is covered by a cover sheet (11).

8. Miniaturized gas chromatograph pursuant to claim 1, wherein the first sheet (6) comprises at least three channels (12), and the second sheet (7) comprises at least two supply channels (13) and two discharge channels (14).

9. Miniaturized gas chromatograph pursuant to claim 1, further comprising a plurality of recesses (16) provided in the circuit board into which a plurality of capillaries (18) are countersunk for the gas flow.

* * * * *

UNITED STATES PATENT AND TRADEMARK OFFICE
CERTIFICATE OF CORRECTION

| | | |
|---|---|---|
| PATENT NO. | : 7,959,865 B2 | Page 1 of 1 |
| APPLICATION NO. | : 10/541145 | |
| DATED | : June 14, 2011 | |
| INVENTOR(S) | : Tobias Schmidt et al. | |

It is certified that error appears in the above-identified patent and that said Letters Patent is hereby corrected as shown below:

On the title page:
Abstract (57),
Line 13, "facing the other side." should read --facing the other sheet.--.

Column 6,
Line 5, "heating is provided" should read --heating element is provided--.
Line 6, "own heating." should read --own heating element.--.
Line 7, "to provided several" should read --to provide several--.

Signed and Sealed this
Nineteenth Day of June, 2012

David J. Kappos
*Director of the United States Patent and Trademark Office*